United States Patent [19]
Dion

[11] Patent Number: 4,523,149
[45] Date of Patent: Jun. 11, 1985

[54] METHOD FOR IDENTIFYING SELECT NON-MAGNETIC MINERALS IN THE PRESENCE OF MAGNETIC MINERALS

[75] Inventor: Eric P. Dion, Dallas, Tex.

[73] Assignee: Mobil Oil Corporation, New York, N.Y.

[21] Appl. No.: 434,445

[22] Filed: Oct. 15, 1982

[51] Int. Cl.³ .............................................. G01V 3/00
[52] U.S. Cl. ................................................... 324/377
[58] Field of Search ........................... 324/377, 345; 209/223.1

[56] References Cited
U.S. PATENT DOCUMENTS 3,432,037  3/1969  Pixley ............................... 209/223

FOREIGN PATENT DOCUMENTS 0212993  2/1958  Australia ........................... 324/345

Primary Examiner—Gerard R. Strecker
Assistant Examiner—Walter E. Snow
Attorney, Agent, or Firm—A. J. McKillop; Michael G. Gilman; George W. Hager, Jr.

[57] ABSTRACT

A sample of an earth formation is subjected to a magnetizing field. The magnetic and non-magnetic fractions of the earth formation sample are separated while under the influence of the magnetizing field. The weights of the magnetic and non-magnetic fractions are measured and the weight percentage of the magnetic fractions determined. The presence or absence of select minerals in the non-magnetic fraction is determined on the basis of the weight percentage of the magnetic fraction.

2 Claims, 2 Drawing Figures

METHOD FOR IDENTIFYING SELECT NON-MAGNETIC MINERALS IN THE PRESENCE OF MAGNETIC MINERALS

BACKGROUND OF THE INVENTION

Heavy minerals, such as platinum and gold, are often found in association with magnetic igneous rocks and are concentrated into placer deposits by chemical and physical weathering processes. Although such heavy minerals are not magnetic in themselves, they are frequently found in surface and subsurface deposits bearing magnetic minerals. For example, it is known that platinum and gold bearing placer mineral deposits often contain magnetite and chromite. The quantity of magnetite and/or chromite can be used as a prospecting guide for deposits enriched in platinum or gold.

Previous prospecting techniques for such heavy minerals have employed geochemical methods, primarily chemical analysis of core samples in the laboratory. Also magnetometers have been used to take advantage of the close association of platinum and gold with magnetite and chromite (See *Introduction to Geophysical Prospecting*, McGraw-Hill Book Company, Inc., New York, 1960, pages 315-316).

SUMMARY OF THE INVENTION

In accordance with the present invention there is provided a method for quantifying select non-magnetic minerals in the presence of magnetic minerals in earth formations.

A sample of an earth formation is subjected to a magnetizing field to attract any magnetic minerals present. The magnetic and non-magnetic mineral fractions of sample are separated while the sample remains under the influence of the magnetizing field. The weights of the magnetic and non-magnetic fractions are measured and the weight percentage of the magnetic fractions determined. The presence of absence of select minerals in the non-magnetic fraction is determined on the basis of the weight percentage of the magnetic fraction.

In a further aspect, the sample is agitated while under the influence of the magnetic field to aid in the separation of the magnetic and non-magnetic functions.

Select non-magnetic minerals, such as platinum and gold, can be identified in specified minimum concentrations when the measured weight percentage of magnetic minerals, such as magnetite and chromite, exceeds a specified percentage level.

DESCRIPTION OF THE PREFERRED EMBODIMENT

In accordance with the present invention, there is provided a method for heavy mineral identification based on magnetic separation.

It has been found that core samples with more than 25% magnetic minerals by weight also contain more than 0.03 parts per million (ppm) platinum. The presence of magnetic minerals above 25% does not specifically quantify platinum content, but it does predict the presence of platinum at a concentration level greater than 0.03 ppm. The magnetic mineral fraction is predominately magnetite with an unknown proportion of chromite. The presence of magnetite and chromite is, therefore, an indication of the presence of platinum.

Figure 1:
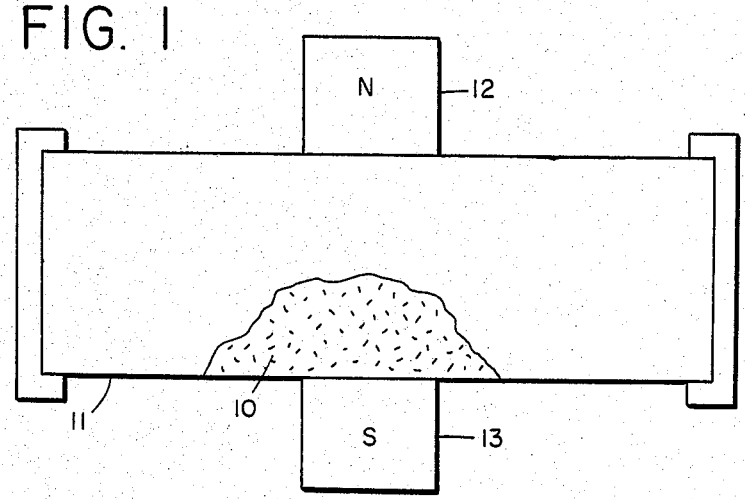
FIG. 1 illustrates a system for magnetizing the magnetic mineral components of a sample of earth formation in accordance with the present invention.
Figure 2:
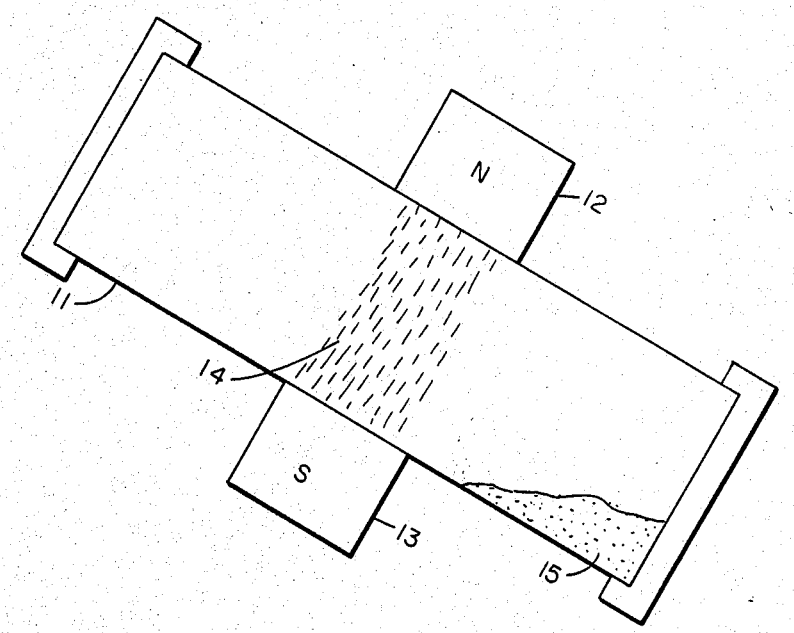
FIG. 2 illustrates a means for separating the magnetized from the non-magnetized mineral components of the earth sample while still under the magnetizing influence of the system of FIG. 1.

Referring now to FIG. 1, an unconsolidated core sample 10 from a surface of subsurface formation is placed in a container 11. Such container contains a mixture of a non-magnetic mineral, such as platinum, and a magnetic mineral, such as magnetite and chromite. The container 11 is then subjected to a magnetizing field from the N and S poles, 12 and 13 respectively, of a permanent or electro-magnet and is agitated. While still under the influence of such magnetizing field, the container 11 may be tilted thereby separating the magnetic and non-magnetic contents, 14 and 15 respectively, as shown in FIG. 3, the magnetic contents 14 being held in place by the magnetizing field between N and S poles 12 and 13 respectively. The weights of the magnetic and non-nonmagnetic portions are then measured and the percentage of the magnetic portion determined. Platinum deposits are then identified as being present when the percentage of associated magnetic material exceeds about 25%. The following table sets forth specific examples of 10 core samples tested for percent magnetic minerals and platinum content.

| SAMPLE | % MAGNETIC MINERALS | PLATINUM (ppm) |
| --- | --- | --- |
| 1 | 67.0 | 1.9 |
| 2 | 50.6 | 0.03 |
| 3 | 49.2 | 2.2 |
| 4 | 42.2 | 1.6 |
| 5 | 35.5 | 0.12 |
| 6 | 25.2 | 0.03 |
| 7 | 7.7 | 0.03 |
| 8 | 7.7 | 0.03 |
| 9 | 6.4 | 0.03 |
| 10 | 4.8 | 0.03 |

It can be seen that the presence of magnetic minerals above about 25% to 30% by weight does not specifically quantify platinum content, but does indicate the presence of platinum at a level greater than 0.03 ppm.

It is to be understood that the foregoing describes one embodiment of the present invention. Various modifications, as well as alternate embodiments, may become apparent to one skilled in the art without departing from the scope and spirit of the invention as hereinafter defined by the appended claims.

I claim:

1. A method for identifying select non-magnetic minerals in the presence of magnetic minerals in earth formations, comprising the steps of:
   (a) obtaining a core sample from an earth formation whose magnetic and non-magnetic material contents all to be determined,
   (b) subjecting said core sample of said earth formation to a magnetizing field to attract said magnetic minerals,
   (c) separating the magnetic and non-magnetic fractions of said sample while said sample is under the influence of said magnetizing field,
   (d) weighing the fractions of said separated magnetic sand on-magnetic fractions,
   (e) determining the weight percentage of said magnetic fraction, and (f) quantifying the abundance of select minerals in said non-magnetic fraction based upon the weight percentage of said magnetic fraction as compared to previous recordings of relative weight percents.

2. The method of claim 1 wherein said select non-magnetic mineral is platinum and the platinum content is identified as being present in concentrations of at least 0.03 parts per million when said magnetic mineral content is at least 25% by weight.

* * * * *